(12) United States Patent
Flores-Valdez et al.

(10) Patent No.: US 7,935,354 B2
(45) Date of Patent: May 3, 2011

(54) **GENERATION OF NEW BCG VACCINE STRAINS PROTECTING AGAINST THE ESTABLISHMENT OF LATENT *MYCOBACTERIUM TUBERCULOSIS* INFECTION AND REACTIVATION FROM THE LATENT OR PERSISTENT STATE**

(75) Inventors: Mario Alberto Flores-Valdez, Jalisco (MX); Gary K. Schoolnik, Palo Alto, CA (US); Michel Klein, Zaandijk (NL); Jerald C. Sadoff, Washington, DC (US); David Hone, Poolesville, MD (US)

(73) Assignees: Aeras Global TB Vaccine Foundation, Rockville, MD (US); The Board of Trustees of the Leland Stanford Junior University, Palo Alto, CA (US)

( * ) Notice: Subject to any disclaimer, the term of this patent is extended or adjusted under 35 U.S.C. 154(b) by 621 days.

(21) Appl. No.: 11/939,144

(22) Filed: Nov. 13, 2007

(65) Prior Publication Data

US 2009/0123492 A1    May 14, 2009

(51) Int. Cl.
 *A61K 39/04* (2006.01)
 *A61K 49/00* (2006.01)
 *A61K 39/00* (2006.01)
(52) U.S. Cl. .................. 424/248.1; 536/23.1; 536/23.7; 424/9.1; 424/9.2; 424/184.1; 424/200.1
(58) Field of Classification Search .................. 424/9.1, 424/9.2, 184.1, 200.1, 248.1; 536/23.1, 23.7
See application file for complete search history.

(56) References Cited

U.S. PATENT DOCUMENTS 6,833,135 B1    12/2004 Pereira

OTHER PUBLICATIONS

Voskuil, M., "Inhibition of Respiration by Nitric Oxide Induces a *Mycobacterium tuberculosis* Dormancy Program", The Journal of Experimental Medicine, vol. 198, No. 5, pp. 705-713, 2003.
Boon, C., "Mycobacterium bovis BCG Response Regulator Essential for Hypoxic Dormancy", Journal of Bacteriology, vol. 184., No. 24, Dec. 2002, pp. 6762-6767.
Park, Heui-Dong., "Rv3133c/dosR is a transcription factor that mediates the hypoxi reponse of *Mycobacterium tuberculois*", Molecular Microbiolgy, 2003, 48(3), pp. 833-843.
Geluk, Annemicke, "T-Cell Recongnition of the HspX Protein of *Mycobacterium tuberculosis* Correlates with Latent M. tuberculosis Infection but Not with M. bovis BCG Vaccination", Infection and Immunity, Jun. 2007, pp. 2914-2921.

*Primary Examiner* — Rodney P. Swartz
(74) *Attorney, Agent, or Firm* — Whitham Curtis Christofferson & Cook, PC

(57) ABSTRACT

A vaccine for treating or preventing the establishment of latent tuberculosis infections is provided. The vaccine comprises a recombinant *mycobacterium* that overexpresses the transcription factor DosR, at a level sufficient to induce production of the dosR regulon genes or proteins. A host to whom the vaccine is administered mounts an immune response to the dosR regulon proteins and is thus protected from the establishment, persistence or reactivation of latent tuberculosis.

6 Claims, 2 Drawing Sheets

A.

VVKVFLVDDHEVVRRGLVDLLGADPELDVVGEAGSVAEAMARVPAARPDVAVLDVRL
PDGNGIELCRDLLSRMPDLRCLILTSYTSDEAMLDAILAGASGYVVKDIKGMELARAVK
DVGAGRSLLDNRAAAALMAKLRGAAEKQDPLSGLTDQERTLLGLLSEGLTNKQIADRM
FLAEKTVKNYVSRLLAKLGMERRTQAAVFATELKRSRPPGDGP

B.
gtggtaaaggtcttcttggtcgatgaccacgaggtggtgcgtcgtggtctggttgacttg
cttggggccgatcccgagcttgacgtcgtaggtgaggcgggttcggtcgccgaggcgatg
gccagggttcctgccgcgcgcccagatgtcgcggtgctggatgtccggttgcccgatggc
aacggcattgaactgtgccgcgatctgttgtcccgcatgcccgatctgcgctgtctgatc
ctcacgtcctacacctctgacgaggccatgctagatgcgattctcgccggtgccagcgga
tatgtcgtcaaagacatcaagggaatggagttggcgcgcgccgtcaaagatgtgggcgct
ggacggtcgctgctggacaatcgggccgcggccgcgctgatggccaagctgcgcggtgcc
gccgagaagcaggacccgctatcaggccttaccgaccaggagcggacgctactgggcctg
cttagcgagggcctgaccaacaagcagatcgccgaccgaatgttcctagccgaaaagacg
gtgaagaactacgtgtcgcggttgctggccaagctgggcatggaacgtcggacgcaagcc
gcggtattcgcgacggagttgaagcgctcgcggccacccggtgatggaccatga

Figure 1A and B

GENERATION OF NEW BCG VACCINE STRAINS PROTECTING AGAINST THE ESTABLISHMENT OF LATENT *MYCOBACTERIUM TUBERCULOSIS* INFECTION AND REACTIVATION FROM THE LATENT OR PERSISTENT STATE

BACKGROUND OF THE INVENTION

1. Field of the Invention

The invention generally relates to a vaccine for treating or preventing the establishment of latent tuberculosis infections. In particular, the invention provides a recombinant *mycobacterium* that overexpresses the transcription factor DosR at a level sufficient to cause induction of the dosR regulon even under non-inducing conditions.

2. Background of the Invention

Tuberculosis (TB) is a global public health problem resulting in 8 million new cases and 2 million deaths each year. An estimated 2 billion persons (one-third of the world's population) are latently infected with *Mycobacterium tuberculosis* (Mtb) Reactivation of latent tuberculosis accounts for most new cases of active disease. Reactivation from latent TB (i.e. active tuberculosis) is associated with inflammation, necrosis and cavitation of the lung, a process that results in draining of the lesions into the bronchus. The resulting cough-generated aerosol causes dissemination of the organism to uninfected, susceptible persons, thus maintaining a transmission chain.

The ability of Mtb to enter a latent state has been investigated. Cole (Nature 393:537-544, 1998) identified a putative phosphorylation-dependant transcription factor Rv3133c that is upregulated immediately upon entry into dormancy. Boon and Dick (J. Bacteriol. 184: 6760-6767, 2002) demonstrated that disruption of dormancy-induced Rv3133c resulted in the loss of the ability of BCG to enter and maintain the dormant state, and that upregulation of several dormancy proteins required the Rv3133c response regulator. Based on these two functions, dormancy survival and regulation, they named the Rv3133c gene dosR for "dormancy survival regulator". The DosR protein is thus a key regulator in the mycobacterial dormancy response. Further investigations (e.g. Voskuil et al., J. Exp Med. 198:705-713, 2003) demonstrated that the induction of a set of 48 genes (including dosR) adapts the Mtb organism for survival during extended periods of dormancy. The 48-gene set is known as the dormancy regulon or dosR regulon.

Current vaccine strategies are focused on the use of the *Bacillus* Calmette-Guérin (BCG) vaccine for the immunization of healthy persons who have never been in contact with *M. tuberculosis*. This strategy has been of questionable efficacy and only addresses stopping active or progressive disease, without taking into account the relevance of the latent, carrier population, particularly in countries where tuberculosis is endemic. Further, the efficacy of BCG is disputed, with various controlled clinical trials and case control studies showing estimates of protection ranging from zero to 83%. A metaanalysis of the results of these trials led one group to conclude that the level of protection against pulmonary tuberculosis was 50% if the effect of latitude was included in a regression model, whereas another group concluded that these data were too heterogeneous for meaningful analysis. Both the meta-analyses concluded that there was significant protection against disseminated forms of disease, such as tuberculous meningitis and miliary tuberculosis, with efficacy estimates ranging between 64% and 86%, but little protection was afforded by BCG vaccination against the development of pulmonary tuberculosis in adolescents or adults (Mahommed et al., Pediatr Infect Dis J., 25(12): 1167-72, 2006). Thus, the efficacy of the current BCG vaccine is debatable.

Most current strategies for the development of new TB vaccines are also focused on preventing active or progressive disease by using attenuated variants of *M. tuberculosis*. Examples include auxotrophs, e.g. for amino acids (Lee et al., Infect Immun., 74(11):6491-6495, 2006; Sampson et al., Infect Immun. 72(5):3031-7, 2004), for nucleotide metabolism (Brown et al, Infect Immun. 2005 January; 73(1):666-70, 2005; Sambandamurthy et al., Nat. Med. 8(10):1171-4, 2002), devoid of transcriptional regulators like PhoP (Martin et al., Vaccine, 24(17):3408-19, 2006) or unable to produce some lipids, like the FadD26 mutant (Infante et al., Clin Exp Immunol., 141(1):21-8, 2005). However, vaccines based on such strategies still do not address the relevance of the persistent stage of tuberculosis.

International patent application publication number WO 2006/104389 (Leiden University Medical Center) does address the relevance of the persistent stage of tuberculosis. However, this application discloses only subsets of dosR regulon latency-associated proteins that are purportedly useful for eliciting an immune response. The application is focused entirely on provision of the proteins as antigens, and DosR is among the antigens that are listed. However, DosR is not a preferred antigen, nor is induction of genes in the dosR regulon suggested or considered.

The prior art has thus far failed to provide a tuberculosis vaccine that provides protection against the development, maintenance and/or reactivation of latent tuberculosis infection, and such a vaccine would be highly beneficial. For example, because reactivation is typically associated with some type of immunosuppressing condition (e.g. diabetes, aging, etc.) that allows a latent lesion to progress to active disease, it would be highly beneficial to have available a vaccine that thwarts this progression, e.g. by promoting elimination of mycobacteria that are in the latent state. No such vaccine is currently available. Further, no current vaccine, and no vaccine under development, is designed to take advantage of the properties of the DosR transcriptional regulator.

SUMMARY OF THE INVENTION

The present invention provides a latency- or persistent-specific tuberculosis vaccine comprising a recombinant *mycobacterium* strain that over-expresses DosR, the latency-specific transcriptional regulator of the dormancy regulon, and thus induces the expression of the DosR regulon. Normally, dormancy regulon expression is restricted to non-replicating bacteria where cell division has been discontinued owing to environmental stimuli such as low oxygen tension or exposure to nitric oxide. However, a genetically engineered BCG strain described herein for exemplary purposes dissociates replication from dormancy regulon expression. Overexpression of DosR causes induction of one or more dormancy regulon genes in replicating bacteria at a level in the range of from 2 to 100 fold above that which would be observed in a non-induced, replicating *mycobacterium*. Any genetically engineered bacterium that overproduces DosR at a level sufficient to cause a 2-100 (or more) fold induction of dosR regulon genes or proteins may be advantageously used in the practice of this invention. When the recombinant *mycobacterium* of the invention is administered to a mammalian host, an immune response is elicited to the proteins encoded by the induced dosR regulon genes. Without being bound by theory, it is believed that mycobacteria that later infect the host will be unable to establish a latent infection in the host; when the proteins required to establish a latent infection are expressed by an infecting *mycobacterium*, they will be recognized by the host immune system and the *mycobacterium* will be destroyed. Alternatively, or in addition, in individuals in which a latent infection is already established, the ability of the mycobacteria to reactivate and progress to active disease is attenuated. In this case, the latent mycobacteria may be eradicated by the immune system, or may simply be unable to emerge from the latent (persistent) state, and confined to a dormant existence. Either way, an active, contagious tuberculosis infection is prevented and the transmission to other humans is halted.

BRIEF DESCRIPTION OF THE DRAWINGS

FIGS. 1A and B. A, Amino acid sequence of an exemplary DosR protein from the *M. tuberculosis* H37Rv dosR (devR) gene, as presented in the genome sequence available at the Pasteur Institutes TubercuList Website (SEQ ID NO: 1); B, nucleic acid sequence encoding the exemplary DosR protein of FIG. 1A (SEQ ID NO: 2).

DETAILED DESCRIPTION OF THE PREFERRED EMBODIMENTS OF THE INVENTION

Figure 2:
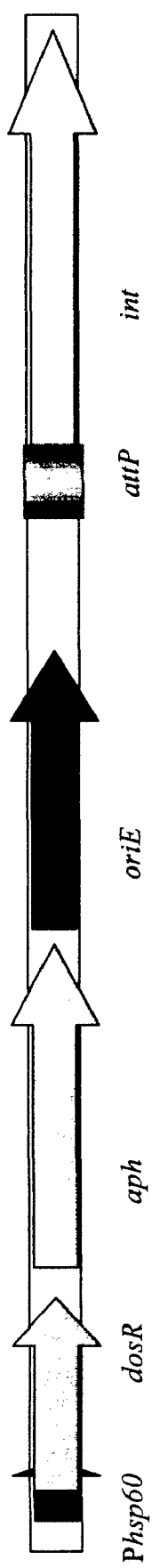
FIG. 2. Schematic representation of the integrative vector for constitutive expression of DosR in Mycobacteria. Phsp60 indicates the 0.4 kb of the 5'-end of the BCG heat shock protein 60 gene locus, to which dosR is fused, and includes the promoter region, ribosome binding site, and first six codons (MAKTIA) of the hsp60 gene, as well as multiple cloning sites and the *E. coli* rrnABt1 transcriptional terminator. The Tn903-derived aph gene (kanamycin resistance) and an origin of replication functional in *E. coli* (oriE) derived from pUC19 are indicated, as well as the attP sequence and int gene from the mycobacteriophage L5, for integration into the attB site of mycobacteria (modified from Stover et al., Nature 6; 351(63261:456-60, 1991).

The present invention provides a vaccine or immune stimulating compositions which includes one or more genetically engineered mycobacteria that over-expresses DosR, the latency-specific transcriptional regulator (transcription factor). Persistent overexpression of DosR results in the production, by the *mycobacterium*, of latency associated genes and translated antigens even though the bacterium has not entered the latent phase. When compositions containing such a *mycobacterium* are administered as a vaccine, the vaccine recipient is therefore exposed to and mounts an immune response to the latency associated antigens being expressed by the bacterium. Without being bound by theory, it is believed that if the vaccinated individual is subsequently exposed to Mtb, the immune system will be able to recognize and destroy bacteria that produce proteins necessary for the establishment and/or maintenance of a latent infection, thereby thwarting development of a persistent infection. Alternatively, for individuals already harboring a latent TB infection, the immune response of a vaccinated individual to DosR regulated gene products may be boosted to recognize and destroy mycobacteria producing proteins necessary for the maintenance of latency. The development of active disease and transmission of the bacterium to others is thus prevented, and the chain of tuberculosis transmission is halted. In addition, in this recombinant *mycobacterium*, DosR induction has been dissociated from bacterial replication. Thus, the *mycobacterium* of the invention replicates normally and produces genes and antigens characteristic of an "active" *mycobacterium*, which may also elicit an immune response.

An exemplary amino acid sequence of DosR is presented in FIG. 1A (SEQ ID NO: 1) and an exemplary nucleotide sequence encoding the same is presented in FIG. 1B (SEQ ID NO: 2). These sequences represent DosR from the *M. tuberculosis* H37Rv dosR (devR) gene, as presented in the genome sequence available at the Pasteur Institute's TubercuList Website. In general, for purposes of the present invention, "DosR" or "DosR protein" refers to the protein sequence presented in SEQ ID NO: 1 or to any other DosR protein sequence as isolated from a natural or wild-type source such as a *mycobacterium*. However, "DosR" is also intended to encompass various variants, analogs or derivatives of such sequences if they possess an equivalent or similar ability to induce the dosR regulon. All such variants are intended to be encompassed in the scope of this invention. For example, those of skill in the art will recognize that many amino acid substitutions may be made in a protein sequence without compromising its ability to carry out its normal function. In particular, conservative amino acid substitutions of amino acids with similar chemical properties may be made (e.g. aliphatic residues may be replaced by other aliphatic residues, negatively charged residues may be exchanged for other negatively charged residues, positively charged residues may be exchanged for other positively charged residues, isosteric residues may be substituted for one another, etc.). In particular for DosR, which is phosphorylated when active, aspartic acid residues that are phosphorylation targets (e.g. Asp 54) may be replaced by glutamic acid residues so as to mimic a permanently phosphorylated (activated) DosR protein. This and other site-directed mutants are also intended to be encompassed by the present invention.

In addition to conservative amino acid substitutions, certain non-conservative amino acid substitutions and other changes to the primary sequence may also be tolerated without disrupting the activity of DosR, and may even increase its activity. For example, non-conservative amino acid substitutions, particularly in regions of the protein that are not actively involved in dosR regulon induction, may be altered. Further, various additions or deletions to the protein may be made without adverse effects, particularly short (e.g. about 25 amino acids or less) deletions or additions may be made. Such changes may be desirable for any of a variety of reasons, e.g. to increase protein activity, stability, solubility, transport, etc.; to decrease susceptibility to proteases; to provide a "tag" or label (e.g. introduction of a tryptophan residue, or of a His tag sequence); etc.

Generally, such variants will exhibit identity with a native, wild-type DosR primary amino acid sequence in the range of about 50-60%, or 60-70%, of preferably about 70-80%, or more preferably about 80-90%, and most preferably in the range of about 90-100%. Those of skill in the art are familiar with methods for the comparison of amino acid sequences and the determination of identity between or among sequences. All such variants may be utilized in the practice of the present invention, so long as sufficient ability to successfully induce the dosR regulon is retained. Those of skill in the art are well-acquainted with procedures for measuring the activity of proteins, and for determining acceptable levels of activity in variant or derivative forms of proteins. For example, the activity of DosR may be measured by determining the capacity of DosR to induce expression of DosR-regulated genes under non-inducing, aerobic, conditions. In general, all DosR variants that are utilized in the practice of the present invention will retain at least about 50%, preferably at least about 60%, more preferably at least about 70%, even more preferably at least about 80%, and most preferably at least about 90-100% (or more) of the activity of native DosR (i.e. the sequence as isolated from a natural, wild-type source, on which the variant is based).

In addition, the invention comprises variants of DosR that do not include the entire protein, but that include critical portions thereof, e.g. domains (such as the DNA binding domain) that are necessary and sufficient to carry out the activity of DosR, i.e., the induction of expression of DosR regulated genes and/or proteins. Variants of these regions are also within the scope of the invention, i.e. sequences that exhibit identity with a native, wild-type DosR primary amino acid sequence in the range of about 50-60%, or 60-70%, of preferably about 70-80%, or more preferably about 80-90%, and most preferably in the range of about 90-100%. In addition, or alternatively, variants that are utilized in the practice of the present invention will retain at least about 50%, preferably at least about 60%, more preferably at least about 70%, even more preferably at least about 80%, and most preferably at least about 90-100% (or more) of the activity of the native DosR region.

FIG. 1B provides an exemplary nucleic acid sequence that may be used to express the DosR protein as depicted in FIG. 1A. However, those of skill in the art will recognize that, due to the redundancy of the genetic code, many other nucleic acid sequences that encode this protein may be designed. Further, "nucleic acids encoding DosR" is intended to include DNA, RNA, and any hybrid or combination thereof. In addition, nucleic acids encoding the variants, derivatives or analogs of DosR, as described above, are also encompassed by the present invention.

In the genetically engineered (i.e. recombinant) *mycobacterium* of the invention, the DosR protein is over-expressed, i.e. the protein is expressed at a level that exceeds that of a suitable control organism, such as the same *mycobacterium* that has not been genetically engineered to over-express DosR. Those of skill in the art are well acquainted with comparative measurements of protein activity, and with the use of suitable standards and controls for such measurements.

The over-expression of DosR in a *mycobacterium* may be carried out by any suitable method known in the art. Generally, the method will involve linking nucleic acid sequences encoding the DosR protein to expression control sequences that are not, in nature, linked to the dosR gene. Those of skill in the art will recognize that many such expression control sequences are known and would be suitable for use in the invention. For example, if constitutive expression of dosR is desired, expression control sequences (e.g. promoters and associated sequences) including but not limited to: *mycobacterium* optimal promoter (mop, George et al., *Biol. Chem.* 270(45):27292-81995, 1995); blaF promoter (Timm et al., *Mol Microbiol.* 12(3):491-504, 1994); hsp60, ace or msp12 promoters; etc., with or without an optimized ribosomal binding site. Alternatively, over-expression of DosR may not be constitutive but may instead be inducible, in response to an environmental cue. For example, expression of the protein may be driven by a promoter that is induced in a particular location or in response to an environmental stimulus, examples of which include but are not limited to: macrophage inducible promoter (which drives expression of genes that are specifically upregulated within the macrophage phagosome, (see Schannapinger et al. *J Exp Med.* 1:198(5):693-704, 2003); acetamidase promoter (Mahenthiralingam et al., J. Gen. Microbiol. 139(3):575-83, 1993), and tetracycline-inducible (Blokpoel et al., Nucl. Acids Res. 33(2):e22, 2005), etc. In addition, promoters from other species may be utilized, examples of which include but are not limited to: various viral promoters, whereby after "gene therapy-like" strategies (e.g. co-inoculation of mycobacteria and an engineered virus) the Mtb antigens are expressed in selected tissues infected by the co-administered virus; etc. As a further alternative, native or naturally occurring dosR expression control sequences may be altered by genetic engineering techniques (e.g. mutations) to function in a manner that results in over-expression of dosR.

Those of skill in the art will recognize that several avenues are available to introduce nucleic acid sequences encoding the DosR protein, in operable linkage with one or more expression control sequences, into a mycobacterial host where over-expression will occur. For example, the sequences may be included in a vector that is subsequently introduced into the *mycobacterium*. Many vectors suitable for containing and expressing genes are known, and include but are not limited to various extra-chromosomal elements such as plasmids, e.g. those comprising the pAL500 origin of replication, modified to augment their copy number; or other plasmids with origins of replication that are or will be developed; or extrachromosomal elements that do not replicate or integrate into mycobacterial genome but provide a suicidal source for homologous recombination to occur; etc. Introduction of such a vector into a *mycobacterium* may be carried out by any of several known methods suitable for that particular vector, including but not limited to electroporation and mycobacteriophage-mediated transduction for homologous recombination. Any expression element may be used to house the DosR-encoding nucleic acids, and may be introduced into the *mycobacterium* by any suitable means, so long as the resultant genetically engineered *mycobacterium* expresses DosR at a level sufficient to induce the dosR regulon. In a preferred embodiment, the vector is a plasmid and the method that is used is electroporation.

In other embodiments of the invention, the DosR protein is over-expressed from the Mtb chromosome. Those of skill in the art will recognize that various molecular biology strategies exist for generating a *mycobacterium* with this property. For example, various mutations may be introduced into the chromosome (randomly or in a directed fashion) that result in over-production of the DosR protein by the bacterium. Alternatively, nucleic acid sequences that include one or more expression control sequences operably linked to nucleic acid sequences encoding DosR may be introduced into the bacterial chromosome, e.g. by transduction with a suicide plasmid with or without a means for counter-selection, to provide sequences for homologous recombination.

Those of skill in the art will recognize that several suitable, BCG strains exist which are suitable for use in the practice of the invention, including but not limited to:

| ATCC ® Number | Description | Designation | Select |
|---|---|---|---|
| 27289 | *Mycobacterium bovis* | BCG, Chicago 1 | [B; BCGT; tice] |
| 27291 | *M. bovis* | | |

| ATCC ® Number | Description | Designation | Select |
|---|---|---|---|
| 35731 | M. bovis | TMC 1002 | [BCG Birkhaug] |
| 35732 | M. bovis | TMC 1009 | [BCG Swedish] |
| 35735 | M. bovis | TMC 1012 | [BCG Montreal; CIP 105920] |
| 35736 | M. bovis | TMC 1013 | [BCG Brazilian] |
| 35737 | M. bovis | TMC 1019 | [BCG Japanese] |
| 35738 | M. bovis | TMC 1020 | [BCG Mexican] |
| 35739 | M. bovis | TMC 1021 | [BCG Australian] |
| 35741 | M. bovis | | [BCG Glaxo] |
| 35742 | M. bovis | TMC 1025 | [BCG Prague] |
| 35744 | | TMC 1029 | [BCG Phipps] |
| 35745 | M. bovis | TMC 1030 | [BCG Connaught] |
| 35746 | M. bovis | TMC 1101 | [BCG Montreal, SM-R] |
| 35747 | M. bovis | TMC 1103 | [BCG Montreal, INH-R; CIP 105919] |
| 35748 | M. bovis | TMC 1108 | [BCG Pasteur SM-R] |
| 27290 | M. bovis | | [BCG Copenhagen H] |
| 19274 | M. bovis deposited as M. tuberculosis subspecies bovis 50 [BCG] | | |
| 19015 | Mycobacterium sp. deposited as M. bovis Karlson and Lessel BCG | | |
| 35733 | M. bovis | TMC 1010 | [BCG Danish, SSI 1331] and |
| 35734 | M. bovis | TMC 1011 | [BCG Pasteur], etc. |

In addition, the recombinant mycobacteria of the invention need not be confined to strains of BCG. Those of skill in the art will recognize that other *Mycobacterium* strains may also be employed, examples of which include but are not limited to: *M. tuberculosis* CDC1551 strain (See, e.g. Griffith et al., Am. J. Respir. Crit. Care Med. August; 152(2):808; 1995), *M. tuberculosis* Beijing strain (van Soolingen et al., J Clin Microbiol. December: 33(12):3234-8, 1995) H37Rv strain (ATCC#:25618), *M. tuberculosis* pantothenate auxotroph strain (Sambandamurthy et al., supra; *M. tuberculosis* rpoV mutant strain (Collins et al., Proc Natl Acad Sci USA. 92(17): 8036; 1995), *M. tuberculosis* leucine auxotroph strain (Hondalus et al., Infect. Immun. 68(5):2888; 2000), etc., or other attenuated and/or recombinant strains derived from *M. tuberculosis*. Other candidate bacteria include other members of the *M. tuberculosis* complex, other mycobacteria (e.g. *M. africanum* or *M. avium* complex bacteria), or other mycobacterial species. Any *mycobacterium* possessing a DosR regulon with significant homology to TB complex organisms may be used in the practice of the invention. In a preferred embodiment of the invention, the recombinant bacteria in which DosR expression is upregulated is a BCG *mycobacterium*, and in particular *M. bovis* BCG strain BCG SSI 1331.

In addition, the vaccine of the invention encompasses vaccines which overexpress one or more dormancy antigens, particularly dormancy antigens that are frequently recognized by otherwise healthy persons with latent tuberculosis. In one embodiment of the invention, the antigens are selected from Rv0079, Rv0080, Rv0081, Rv0569, Rv0570, Rv0571c, Rv0572c, Rv0573c, Rv0574c, Rv1733c, Rv1734c, Rv1735c, Rv1736c, Rv1737c, Rv1738, Rv1812c, Rv1813c, Rv1996, Rv1997, Rv1998, Rv2003c, Rv2004c, Rv2005c, Rv2006, Rv2007c, Rv2028c, Rv2029c, Rv2030c, Rv2031c, Rv2032, Rv2623, Rv2624c, Rv2625c, Rv2626c, Rv2627c, Rv2628, Rv2629, Rv2630, Rv2631, Rv3126c, Rv3127, Rv3128c, Rv3129, Rv3130c, Rv3131, Rv3132c, Rv3133c and Rv3134c. In particular, such antigens may include, for example, Rv0079, Rv0569, Rv0572c, Rv1733c, Rv1738, Rv1813c, Rv1996, Rv2007c, Rv2030c, Rv2031c, Rv2032, Rv2623, Rv2624c, Rv2626c, Rv2627c, Rv2628, Rv3126c, Rv3127, Rv3129, Rv3130c, Rv3131, Rv3132c, Rv3133c and Rv3134c.

In yet another embodiment, the vaccine of the invention may be a subunit or DNA-vaccine. In some embodiments, the vaccine would be delivered via lung pathogens, For example, the DNA sequences coding for DosR and DosR antigens could be harbored within the chromosome or extrachromosomal nucleic acid of a lung pathogen such as attenuated *Pseudomonas aeruginosa*, or other known attenuated fungi or viruses. Alternatively, the nucleic acid encoding DosR and DosR antigens could be delivered by other means known to those of skill in the art, e.g. via liposomes, adenoviral vectors, etc.

The present invention further provides compositions for use in eliciting an immune response in and/or vaccinating a mammal. The compositions may be utilized as a vaccine against Mtb, particularly against latent forms of Mtb, or forms of Mtb that are entering or emerging from latency. The compositions of the invention include genetically engineered mycobacteria as described herein, alone or in combination with a pharmacologically suitable carrier. The preparation of such compositions for use as vaccines is well known to those of skill in the art. Typically, such compositions are prepared either as liquid solutions or suspensions, however solid forms such as tablets, pills, powders and the like are also contemplated. Solid forms suitable for solution in, or suspension in, liquids prior to administration may also be prepared. The preparation may also be emulsified. The active ingredients may be mixed with excipients which are pharmaceutically acceptable and compatible with the active ingredients. Suitable excipients are, for example, water, saline, dextrose, glycerol, ethanol and the like, or combinations thereof. In addition, the composition may contain minor amounts of auxiliary substances such as wetting or emulsifying agents, pH buffering agents, and the like. In addition, the composition may contain other adjuvants. If it is desired to administer an oral form of the composition, various thickeners, flavorings, diluents, emulsifiers, dispersing aids or binders and the like may be added. The composition of the present invention may contain any such additional ingredients so as to provide the composition in a form suitable for administration. The final amount of recombinant mycobacteria in the formulations may vary. However, in general, the amount in the formulations will be from about 1-99%. The compositions may further comprise additional adjuvants, suitable examples of which include but are not limited to Seppic, Quil A, Alhydrogel, etc.

Vaccine formulation also involves studies to determine maximum bacterial viability and stability throughout the manufacturing process. This includes determination of maximum organism viability (live to dead) during culture utilizing a variety of commonly used medium for the culture of mycobacteria to include the addition of glycerol, sugars, amino acids, and detergents or salts. After culture, cells are harvested by centrifugation or tangential flow filtration and resuspended in a stabilizing medium that allows for protection of cells during freezing or freeze-drying process. Commonly used stabilizing agents include sodium glutamate, or amino acid or amino acid derivatives, glycerol, sugars or commonly used salts. The final formulation will provide sufficient viable organism to be delivered by intradermal, percutaneous injection, perfusion or oral delivery with sufficient stability to maintain and adequate shelf life for distribution and use.

The methods of the present invention preferably involve administering a composition comprising the recombinant mycobacteria of the invention in a pharmacologically acceptable carrier to a mammal, which is usually, but not always, a human. The vaccine preparations of the present invention may be administered by any of the many suitable means which are well known to those of skill in the art, including but not limited to by injection, orally, intranasally, by ingestion of a food product containing the antigen, by inhalation, etc. In preferred embodiments, the mode of administration is intradermal or oral. In addition, the compositions may be administered alone or in combination with other medicaments or immunogenic compositions, e.g. as part of a multi-component vaccine. Further, administration may be a single event, or multiple booster doses may be administered at various timed intervals to augment the immune response.

A particular advantage of the vaccine preparation of the present invention is that while administration may be prophylactic (i.e. before exposure to the bacteria has occurred, or is suspected to have occurred) but may also be after the fact (i.e. after a known or suspected exposure) or therapeutically (i.e. after the occurrence of indicators associated with latent bacterial infection). Thus, the vaccine is useful not only for preventing an initial active Mtb infection, but also for preventing the establishment, persistence or reactivation of a latent Mtb infection.

Prior to administration to humans as a vaccine, the genetically engineered mycobacterial strains of the present are tested according to methods that are well-known to those of skill in the art. For example, tests for toxicity, virulence, safety, etc. are carried out in suitable animal models, e.g. in mice, guinea pigs, etc., some of which are immunocompromised. The ability of the vaccine preparations to elicit an immune response is likewise typically tested in suitable animal models, e.g. mice, non-human primates, etc. In addition, protection studies involving vaccination, boosting, and subsequent challenge with live Mtb may be carried out using suitable animal models such as mice, guinea pigs, and non-human primates. Finally, those of skill in the art are familiar with the arrangements for carrying out clinical trials in consenting humans, in order to test the efficacy of the vaccine preparations. For details, see, for example, United States patent application 20060121054 (Sun et al.) published Jun. 8, 2006, which is hereby incorporated by reference, and references cited therein.

The present invention also provides methods of eliciting an immune response to one or more of the dosR regulon proteins, which include: Rv0079, Rv0080, Rv0081, Rv0569, Rv0570 (nrdZ), Rv0571c, Rv0572c, Rv0573c, Rv0574c, Rv1733, Rv1734c, Rv1735c, Rv1736c (narX), Rv1737c (nark2), Rv1738, Rv1812c, Rv1813c, Rv1996, Rv1997 (ctpF), Rv1998c, Rv2003c, Rv2004c, Rv2005c, Rv2006 (otsB1), Rv2007c (fdxA), Rv2028c, Rv2029c (pfkB), Rv2030c, Rv2031c (acr), Rv2032 (acg), Rv2623, Rv2624c, Rv2625c, Rv2626c, Rv2627c, Rv2628, Rv2629, Rv2630, Rv2631, Rv3126c, Rv3127, Rv3128c, Rv3129, Rv3130, Rv3131, Rv3123c, Rv3133c (dosR) and Rv3134c.

By "eliciting an immune response" we mean that administration of the vaccine preparation of the present invention causes the synthesis of specific antibodies (at a titer in the range of 1 to $1 \times 10^6$, preferably $1 \times 10^3$, more preferable in the range of about $1 \times 10^3$ to about $1 \times 10^6$, and most preferably greater than $1 \times 10^6$) and/or cellular proliferation, as measured, e.g. via cellular assays in which IFN-γ production is assessed, by $^3$H thymidine incorporation, etc. In addition, to measure humoral immune responses, a peptide microarray chip may be used. The peptide array is spotted with overlapping 50 amino acid peptides generated from the sequences of all BCG encoded DosR-regulated proteins which are at least 2 fold induced by the overexpression of DosR. Pooled sera from each group of vaccinated individuals is incubated with 3 peptide chips for 1 hr at 37° C. The chips are then washed with phosphate-buffered saline (PBS) pH7.2 and incubated with fluorescein isothiocyanate (FITC) conjugated goat anti-mouse IgG sera (Abcam, Cambridge, Mass.) for 1 hour at 37° C. The chips are then washed again with PBS and the immunofluorescence is read with a Genepix 4000B Array Scanner (Molecular Devices, Sunnyvale, Calif.). Values for each peptide spot are averaged for the 3 chips in each group. Vaccinated subjects would show higher titre responses than non-vaccinated or BCG vaccinated controls. Further, to measure cellular immune responses elicited by DosR regulon expressing vaccines, splenocytes or peripheral blood mononuclear cells (PBMC's) from vaccinated subjects are incubated with Rv2623 and Rv3130c as these proteins are known to be highly upregulated in DosR overexpressing strains and are known to be potent T cell immunogens. After the 3 day incubation, supernatants are harvested from the splenocyte cultures and assayed by enzyme-linked immunosorbent assay (ELISA) for interferon-γ produced in response to antigen stimulation. Control cultures of unstimulated splenocytes/PBMC's or phytohemagglutinin (PHA) and phorbol myristate acetate (PMA) stimulated splenocytes/PBMC's are included as negative and positive controls, respectively.

In a preferred embodiment, the immune response is a protective immune response, i.e. the immune response protects the vaccinated individual from future challenge with Mtb. The methods involve administering a composition comprising a mycobacterial strain of the present invention in a pharmacologically acceptable/compatible carrier.

In preferred embodiments of the invention, the dosR regulon proteins that are produced are those that are most highly induced, that elicit a strong IFN-γ response, that are potent T cell or B cell immunogens, and possess high sequence homology to their Mtb homologue. In particular, this would likely include bacterial components that are readily accessible to cells of the immune system (e.g. surface exposed) that elicit such IFN-γ release with no effect upon production of anti-inflammatory molecules.

The dosR regulon genes that are expressed or proteins which are transcribed in response to DosR induction are produced at a level that is in the range of from about 2 to about 100 fold greater than the level that is observed in a *mycobacterium* in which DosR is not over-expressed, e.g. a control or wild type aerobically replicating *mycobacterium*. In the practice of this invention, this overproduction of gene products, as measured by transcription, or antigens translated from the transcribed genes, is what is meant by induction. Preferably, the fold increase is from about 2-10, or 10-20, or 20-30, or 30-40, or 40-50, or 50-60, or 60-70, or 70-80, or 80-90, or 90-100, or even more than a 100 fold increase is observed. According to the invention, at least one of the 48 dosR regulon genes (and presumably the encoded protein) is produced at this level, and preferably from about 1-5, or 5-10, or 10-15, or 15-20, or 20-25, or 25-30, or 30-35, or 35-40, or 40-45, or up to all 48 of the genes are expressed at this increased level.

In addition, a recombinant strain of the invention may be used as a tool to specifically diagnose people latently infected with *Mycobacterium tuberculosis*. In this embodiment, recombinant BCG overexpressing DosR-antigens are cultivated under non-inducing conditions to prepare whole cell extracts, and the IFN-γ, cell-mediated response is compared to that of wild type BCG or Mtb to distinguish between people with active and latent Mtb infection.

EXAMPLES

Example 1

Construction of a BCG Strain Constitutively Expressing the Latency-Specific Transcriptional Regulator, dosR In order to construct a BCG strain (*M. bovis* BCG SSI 1331) constitutively expressing the latency-specific transcriptional regulator, DosR (also known as DevR and Rv3133c), a vector was constructed in which dosR was expressed under the control of the hsp60 promoter. In order to do so, the wild-type *M. tuberculosis* dosR gene was amplified from Mtb strain 1254 using the primers devR-FPvu2 (5'GTG-CAGCTGTCATGGTAAAG GTCTTCTTGGTCG-3, SEQ ID NO: 3) and devREHd3 (5'-ACTAAGCTTCCTGTTGTC ATGGT CCATCACCG-3, SEQ ID NO: 4). The devR-FPvu2 primer was designed so that it maintains the correct Open Reading Frame (ORF) in the vector, under the control of the hsp60-promoter, and so that it includes a change in the start codon of dosR from GTG to ATG. The 216 amino acids residues encoded by the PCR product are identical to those encoded by the *M. tuberculosis* H37Rv dosR (devR) gene, as presented in the genome sequence available at the TubercuList Website located at genolist.pasteur.fr.

The PCR reaction was performed using Platinum Pfx High Fidelity Supermix (Invitrogen) and genomic DNA from wild-type *M. tuberculosis* 1254 as a template. The resulting PCR products were cloned into a pCR4 vector plasmid, using a TOPO cloning system (Invitrogen). The resulting plasmid is depicted schematically in FIG. 2. After transformation into an *E. coli* host, selection of recombinant clones was accomplished by growing colonies on Luria broth (LB) plates containing 50 μg/mL of kanamycin. Plasmid DNA from selected clones was isolated and sequenced, and one plasmid containing an insert with a sequence 100% identical to that of wild type *M. tuberculosis* H37Rv dosR was selected for further work. A PvuII/HindIII fragment of the plasmid, which encompassed the cloned dosR, was subcloned into pMV361, a kanamycin resistant, integrative shuttle vector, thereby creating a plasmid designated pMF361dosR. The genetic makeup of pMF361dosR was confirmed by restriction digestion and sequencing.

Generation of a BCG recombinant strain was accomplished as follows: *M. bovis* BCG SSI 1331 cells were transformed with plasmid pMF361dosR by electroporation, and electroporated cells were plated onto 7H10 media plates supplemented with OADC (Difco) and 25 μg/mL of kanamycin. After 4 weeks of growth, cells from individual clonal colonies were selected and grown in liquid 7H9 media supplemented with ADC (Difco) plus 25 μg/mL of kanamycin. After culturing for 3 weeks in this media, genomic DNA from the selected clones was isolated and checked for the integration of pMF361dosR into the BCG genomic attB site. This was done by PCR using primers that anneal within the vector sequence. All the colonies gave a PCR product of a size indicative of the integration of the construct, thus constituting the new recombinant strain BCG SSI1331::DosR. Aliquots of BCG SSI1331::DosR were subsequently made by mixing 1 mL of culture with 1 mL of 50% sterile glycerol solution, which were stored at −80° C.

The same process was followed in order to obtain *M. tuberculosis* strains that constitutively express DosR (Mtb 1254::DosR, H37Rv::DosR, and H37RvΔRv3132c-Rv3134c::DosR strains). Constitutive production of DosR by the recombinant strain (as measured by the capacity of DosR to induce expression of DosR-regulated genes under non-inducing, aerobic, conditions) was documented by comparing the transcriptional profiles of BCG SSI1331::DosR and wild type BCG SSI1331 grown in vitro. The strains were assayed for dosR induction at early, mid-log and stationary phase during growth in 7H9 ADC 0.05% Tween 80 liquid media, at 37° C., 100 rpm, and 5% $CO_2$. A statistical (SAM) analysis of expression data from BCG strains containing pMV361 vector or the dosR bearing plasmid pMF361dosR, versus BCG wild type, was carried out and the results are presented in Table 1. The results showed that the recombinant strain carrying the dosR bearing plasmid displayed constitutive DosR production (lanes labeled "DosR-OX") whereas BCG cells carrying only plasmid pMV361 (lanes labeled "vector") did not induce DosR-regulated genes, when compared to wild type expression.

In vitro, dosR is induced either by growing *M. tuberculosis* under hypoxic conditions or exposing the microorganism to nitric oxide treatment (Voskuil et al., supra); ex vivo, dosR is activated during macrophage infection (Schnappinger et al., supra). In order to compare induction values, data from day 4 of in vitro dormancy experiments is also included in Table 1 (lane labeled "H37Rv dormancy"). The number of DosR binding sites present (in strain Park MM03) is given in the last column.

TABLE 1

Differential regulation of the DosR-regulon genes

| | Vector | DosR-OX | Vector | DosR-OX | Vector | DosR-OX | BCG WT H37Rv | DosR binding |
|---|---|---|---|---|---|---|---|---|
| | OD600 nm | | | | | | | |
| Gene | 0.2 | 0.2 | 0.4 | 0.4 | 0.8 | 0.8 | Dormancy | sites |
| Rv0079 | 0.89 | 11.89 | 1.19 | 11.32 | 0.93 | 12.71 | 16 | 1 |
| Rv0080 | 1.00 | 4.32 | 0.88 | 3.48 | 0.99 | 3.62 | 11.1 | 0 |

TABLE 1-continued Differential regulation of the DosR-regulon genes

| Gene | Vector 0.2 | DosR-OX 0.2 | Vector 0.4 | DosR-OX 0.4 | Vector 0.8 | DosR-OX 0.8 | BCG WT H37Rv Dormancy | DosR binding sites |
|---|---|---|---|---|---|---|---|---|
| Rv0081 | 0.86 | 2.15 | 1.08 | 1.88 | 1.02 | 1.43 | 7.2 | 0 |
| Rv0569 | 0.87 | 27.06 | 1.01 | 18.09 | 1.04 | 25.52 | 9 | 0 |
| Rv0570 (nrdZ) | 1.04 | 5.40 | 0.96 | 4.74 | 0.93 | 5.17 | 8.3 | 0 |
| Rv0571c | 1.03 | 1.47 | 1.06 | ND* | 1.04 | 1.06 | 2.5 | 1 |
| Rv0572c | 1.09 | 5.52 | 0.98 | 5.40 | 1.06 | 7.18 | 6.7 | 0 |
| Rv0573c | 0.95 | 1.74 | 1.02 | 1.97 | ND | 1.47 | 1 | NR** |
| Rv0574c | 1.05 | 1.55 | 0.99 | 2.10 | 0.95 | 2.57 | 5 | 1 |
| Rv1733c | 0.96 | 30.75 | 1.05 | 22.82 | 1.37 | 1.97 | 6 | 3 |
| Rv1734c | 1.03 | 1.48 | 0.81 | 1.60 | ND | 1.59 | 1.9 | 1 |
| Rv1735c | 0.92 | 1.65 | 1.02 | 1.09 | 0.92 | 1.39 | 1.8 | NR |
| Rv1736c (narX) | 0.98 | 1.00 | 0.75 | 0.79 | ND | 1.06 | 8.1 | 0 |
| Rv1737c (narK2) | 0.95 | 1.02 | 0.79 | 0.93 | 0.89 | 1.28 | 5 | 3 |
| Rv1738 | 0.98 | 22.66 | 0.99 | 16.11 | 0.69 | 19.39 | 24 | 3 |
| Rv1739c | 0.98 | 0.92 | 0.97 | 0.99 | 1.03 | 0.96 | ND | NR |
| Rv1812c | 1.04 | 7.17 | 0.99 | 8.35 | 0.90 | 8.35 | 7.8 | 0 |
| Rv1813c | 0.88 | 43.53 | 0.98 | 27.92 | 0.88 | 32.79 | 22 | 1 |
| Rv1996 | 1.00 | 20.25 | 0.90 | 21.44 | 1.11 | 1.92 | 5 | 1 |
| Rv1997 (ctpF) | 1.00 | 23.58 | 0.93 | 15.42 | ND | 32.87 | 9.4 | 0 |
| Rv2003c | 0.93 | 6.99 | 0.91 | 6.68 | 0.95 | 10.31 | 6 | 0 |
| Rv2004c | 0.96 | 9.82 | 0.87 | 7.64 | 0.92 | 12.27 | 8 | 0 |
| Rv2005c | 0.87 | 14.22 | 1.02 | 12.05 | 1.00 | 14.90 | 11.1 | 1 |
| Rv2006 (otsB) | 0.97 | 5.01 | 0.95 | 3.84 | 1.07 | 4.18 | 2.6 | 1 |
| Rv2007 (fdxA) | 0.87 | 26.40 | 1.06 | 19.57 | 0.68 | 14.76 | 18 | 1 |
| Rv2028c | 0.97 | 9.75 | 0.96 | 13.61 | ND | 29.69 | 17.3 | 0 |
| Rv2029c (pfkB) | 1.12 | 26.25 | 1.06 | 19.65 | 1.24 | 35.60 | 23 | 0 |
| Rv2030c | 1.12 | 68.24 | 0.70 | ND | ND | 58.28 | 48 | 0 |
| Rv2031c (acr) | 0.81 | 57.02 | 1.23 | 35.57 | 0.80 | 37.97 | 31 | 2 |
| Rv2032 | 0.98 | 48.01 | ND | 50.74 | ND | ND | 24 | 2 |
| Rv2033c | 1.12 | 1.74 | 1.06 | 1.29 | 1.02 | 1.56 | ND | NR |
| Rv2623 | 0.92 | 3.58 | 1.01 | 3.13 | 0.92 | 3.45 | 27.3 | 0 |
| Rv2624c | 0.98 | 10.08 | 1.30 | 6.54 | ND | 7.56 | 5 | 0 |
| Rv2625c | 0.86 | 0.69 | 0.83 | 4.83 | 0.88 | 8.27 | 5.3 | 0 |
| Rv2626c | 0.97 | 51.41 | 1.18 | 29.41 | 0.75 | 31.12 | 57 | 2 |
| Rv2627c | 0.92 | 43.79 | 0.97 | 32.29 | ND | 26.72 | 15 | 2 |
| Rv2628 | 1.01 | 36.61 | 1.10 | 29.54 | 0.93 | 42.64 | 23.1 | 2 |
| Rv2629 | 0.87 | 6.90 | 0.96 | 6.35 | 0.86 | 11.07 | 7.7 | 0 |
| Rv2630 | 0.92 | 8.86 | 1.03 | 8.51 | 1.12 | 15.61 | 16.2 | 0 |
| Rv2631 | 0.92 | 3.03 | 0.97 | 2.77 | 1.00 | 4.55 | 6.2 | 0 |
| Rv3126c | 1.03 | 5.97 | ND | 3.03 | 0.99 | 3.46 | 2 | 0 |
| Rv3127 | 0.85 | 35.08 | ND | 24.46 | 0.86 | ND | 21 | 2 |
| Rv3128c | 0.93 | 1.73 | 0.89 | 1.26 | 1.03 | 2.06 | 2 | 0 |
| Rv3129 | 1.00 | 1.27 | 0.92 | 1.25 | 1.04 | 1.14 | 3 | 0 |
| Rv3130c | 1.03 | 18.69 | 0.99 | 14.88 | 0.96 | 15.81 | 28 | 1 |
| Rv3131 | 1.00 | 61.23 | 1.04 | 43.79 | 0.59 | 51.15 | 40.4 | 1 |
| Rv3132c (dosS) | 1.11 | 11.30 | 1.18 | 14.22 | 1.19 | 18.48 | 12.7 | 0 |
| Rv3133c (dosR) | 1.08 | 16.36 | 1.08 | 12.58 | 1.09 | 18.38 | 12 | 0 |
| Rv3134c | 0.98 | 38.32 | 0.99 | 33.24 | 1.13 | 35.46 | 23 | 2 |

The numbers indicate the fold-change in the expression of a particular gene in comparision to the strain containing only pMV361 (vector control). For the experiments with BCG WT, all the samples correspond to cultures at the corresponding $OD_{600}$ nm as reference. For the H37Rv data, the reference is mid-log phase aerobic culture as reported by Voskuil et al., supra. Numbers in bold indicate genes for which expression in the recombinant strain was higher than that observed in reference strain.
*ND indicates a value that was not significantly different between the recombinant strain and the reference.
**NR stands for "not reported".

We further demonstrated that hsp60-driven DosR was active by comparing the transcriptional profile of BCG SSI1331::DosR to that of H37RvΔRv3132c-Rv3134c, a strain lacking dosR (Table 2). The strains were grown in vitro in 7H9ADC media plus 0.05% Tween 80 at 37° C. and 100 rpm, with samples taken at $OD^{600}$ nm=0.4. Statistical (SAM) analysis of the results are presented in Table 2. In this study, the *M. tuberculosis* H37Rv:.DosR strain also showed constitutive expression and activity of DosR (Table 2). The induction values for most of the genes of the DosR regulon are very similar between *M. tuberculosis* H37Rv and *M. bovis* BCG SSI 1331.

TABLE 2

Genes of the dosR regulon that are differentially regulated

| Gene | H37Rv::DosR vs dosRKO | BCG::DosR vs dosRKO |
|---|---|---|
| Rv0079 | 20.5 | 11.81 |
| Rv0080 | 5.7 | 3.2 |
| Rv0081 | 2.2 | 3.7 |
| Rv0569 | 10.5 | 14.3 |
| Rv0570 (nrdZ) | 8.6 | 4.9 |
| Rv0571c | 2.5 | 2.2 |
| Rv0572c | 10.6 | 6.3 |
| Rv0573c | 1.8 | 2 |
| Rv0574c | 2.6 | 2.7 |
| Rv1733c | 18.9 | 18 |
| Rv1734c | 1.2 | 1.2 |
| Rv1735c | 3.4 | 1.5 |
| Rv1736c (narX) | 23.6 | 0.9 |
| Rv1737c (narK2) | 26.1 | 1.2 |
| Rv1738 | 158.7 | 24.1 |
| Rv1739c | 1 | 1.6 |
| Rv1812c | 19.4 | 12.3 |
| Rv1813c | 72.5 | 15.5 |
| Rv1996 | 28.2 | 28.4 |
| Rv1997 (ctpF) | 8.2 | 14.3 |
| Rv2003c | 5 | 6.9 |
| Rv2004c | 13.6 | 16.1 |
| Rv2005c | 14.9 | 13.1 |
| Rv2006 (otsB) | 4.5 | 3.5 |
| Rv2007 (fdxA) | 65.7 | 15.7 |
| Rv2028c | 3.3 | 42.9 |
| Rv2029c (pfkB) | 69.6 | 25.3 |
| Rv2030c | 126.6 | 50.1 |
| Rv2031c (acr) | 111.7 | 30.9 |
| Rv2032 | 90.7 | 22.2 |
| Rv2033c | 1.2 | 2.1 |
| Rv2623 | 3.7 | 3.9 |
| Rv2624c | 26.4 | 6.4 |
| Rv2625c | 14.4 | 7.6 |
| Rv2626c | 99.2 | 35.1 |
| Rv2627c | 52.1 | 27.3 |
| Rv2628 | 46.8 | 40.7 |
| Rv2629 | 12.2 | 13.2 |
| Rv2630 | 13.9 | 15.7 |
| Rv2631 | 2.6 | 2.9 |
| Rv3126c | 2 | 3.4 |
| Rv3127 | 58.7 | 24.1 |
| Rv3128c | 2.8 | 1.8 |
| Rv3129 | 5.7 | 2.4 |
| Rv3130c | 76.4 | 46.8 |
| Rv3131 | 39.9 | 38.1 |
| Rv3132c (dosS) | 87.4 | 29.1 |
| Rv3133c (dosR) | 47.8 | 19.4 |
| Rv3134c | 113.7 | 56.6 |

The numbers indicate the fold-change in the expression of a particular gene in comparison to the strain containing neither pMV361 nor pMF361dosR. For these experiments, all the samples correspond to cultures at the corresponding $OD^{600}$ nm as reference.

This example demonstrates that stable and constitutive expression of DosR was obtained under non-inducing conditions, and that such constitutively produced DosR was able to activate genes of the DosR-regulon despite the presence or absence of the chromosomally encoded copy of this gene.

Example 2

Alternate Recombinant Mycobacterial Strain Producing a Mutant Copy of DosR

Most structure function studies of response regulators have concluded that these proteins adopt a variety of conformations in the cytosol, oscillating between promoter activating configurations and various other configurations which are inert. Phosphorylation of the active site Asp effects a conformational change that favors the promoter activating conformation. In most natural systems, dephosphorylation follows thus preventing constitutive overexpression. Consequently, sustained activation of a response regulator requires continuing phosphorylation by the cognate sensor histidine kinase, which in turn requires that it be continuously autophosphorylated by the activating ligand, present in concentrations that exceed some threshold level. This leads to a strategy for effecting the sustained activation of DosR by generating site directed mutations of the active site Asp (Asp 54) that favor the promoter activating configuration.

Active Site Mutations

A constitutive gain-of-function mutation is sought by mutating the DosR active site Asp (Asp54) to Glu. Glu is isosteric with phosphorylated Asp and thus the protein carrying this mutation may behave as though it is phosphorylated. This strategy has proven to be effective for at least three response regulators: OmpR, NtrC and RcsB.

The active site constitutive mutant is produced as a single copy gene driven by the hsp60 promoter and integrated (together with a selectable antibiotic or other marker) into the chromosome at the attB site. This prevents loss of the gene, a possible consequence complicating the expression of the constitutive mutant from a multicopy, episomal, plasmid. The recipient strain that is used is a deletion mutant of wild type DosR to facilitate evaluation of the mutant and to prevent competition between the wild type DosR protein and the mutant protein for the same promoter sequence or possible dominant-negative effects that might occur if both wild type and mutant protein interact in the cytosol.

A minimum of three variants of the same stain (the BCG wild type parent, BCG dosR deletion mutant and the BCG dosR deletion mutant complemented by the dosR activating mutation) are assessed for expression of the dormancy regulon under two in vitro conditions of growth. Condition 1: In well-stirred (i.e., oxygenated) mid-log phase cultures in 7H9 medium where prior studies have shown the dormancy regulon to be silent. Under this condition, the DosR regulon is silent in the BCG wild type strain and in the dosR deletion mutant, but expressed in the dosR deletion mutant complemented by the activating dosR mutation. Condition 2: In the Wayne low $O_2$ model of latency (day 10) where prior studies of Mtb have demonstrated strong induction of the dormancy regulon. Under this condition, the DosR regulon is expressed by the BCG wild type strain and by the dosR deletion mutant complemented by the activating dosR mutation. By contrast, the dormancy regulon is silent in the dosR deletion mutant.

Regulon induction is monitored by microarray expression profiling. The MTB oligonucleotide microarray is used to assess expression of the BCG dormancy regulon because the nucleotide sequences of 25 of the 48 BCG genes are absolutely conserved with the corresponding H37Rv MTB gene; 15 have a single SNP; five have 2 SNPs; and, two have 3 SNPs when compared to the sequenced MTB strain from which the microarray was derived. In each case, the gene expression profile is compared using two MTB reference RNAs: RNA from MTB strain H37Rv aerated mid log phase cultures in 7H9 medium (this reference represents basal levels of dormancy regulon expression); and RNA from H37Rv low oxygen Wayne model cultures (this reference represents maximal levels of dormancy regulon expression). If more quantitative comparisons of mRNA abundance for a particular dormancy regulon gene is required, quantitative RT PCR methods are employed. The dynamic range of acr transcript and Acr/HspX protein abundance, between basal and maximal levels of expression, are the greatest of any of the dormancy regulon genes. Therefore, as an estimate of dormancy regulon protein expression by the constitutive gain-of-function DosR mutant, serial 10-fold dilutions of a monoclonal antibody to the α-crystallin (acr) protein are used to monitor its expression using western immunoblots.

Example 3

Determination of the Capacity of the Engineered BCG Strain to Engender an Immune Response to Dormancy Regulon Proteins in Mice and the Protective Efficacy of Said rBCG The capacity of the parental BCG and engineered strain to elicit a cellular immune response is compared to dormancy regulon protein in mice. To illustrate the immune responses elicited by BCG-DosR and to demonstrate its protective efficacy against tuberculosis, four groups of 10 C57/BL6 mice are vaccinated subcutaneously with either 1) saline, 2) BCG, 3) BCG-DosR. Mice in groups 2, 3, and 4 receive $5\times10^5$ cfu of BCG or recombinant BCG. After 10 weeks, five mice from each group are sacrificed for immune assays and the remaining animals are challenged with 100 cfu aerosolized *M. tuberculosis* Erdman.

To measure humoral immune responses, a peptide microarray chip is utilized. The chip is spotted with overlapping 50 amino acid peptides generated from the sequences of all BCG encoded DosR-regulated proteins which are at least 2 fold induced by the overexpression of DosR. Pooled sera from each group is incubated with 3 peptide chips for 1 hr at 37.degree. C. The chips are then washed with phosphate-buffered saline (PBS) pH7.2 and incubated with FITC conjugated goat anti-mouse IgG sera (Abeam, Cambridge, Mass.) for 1 hour at 37.degree. C. The chips are then washed again with PBS and the immunofluorescence is read with a Genepix 4000B Array Scanner (Molecular Devices, Sunnyvale, Calif.). Values for each peptide spot are averaged for the 3 chips in each group. Mice receiving BCG-DosR show greater antibody responses to peptides derived from DosR regulated proteins than unvaccinated mice or mice vaccinated with BCG or BCG-PfoA.

To measure cellular immune responses elicited by BCG-DosR, spleens are harvested from each and homogenized. Splenocyte concentrations are adjusted to $5\times10^5$ cells/well in R10 media in multichamber plates and are incubated for 3 days at 37° C. with purified Rv2623 and Rv3130c at 1 μg/ml as these proteins are known to be highly upregulated in DosR overexpressing strains and are known to be potent T cell immunogens. After the 3 day incubation, supernatants are harvested from the splenocyte cultures and assayed by ELISA for interferon-γ produced in response to antigen stimulation. Control cultures of unstimulated splenocytes or PMA/PHA stimulated splenocytes are included as negative and positive controls, respectively.

To quantify protection afforded by vaccination with BCG-DosR, the 5 remaining mice from each group are sacrificed 10 weeks after challenge with *M. tuberculosis* and lungs and spleens are aseptically harvested from each animal. Lungs and spleens are homogenized in PBS and dilutions are plated on 7H10 agar. After 4 weeks of incubation, the number of *M. tuberculosis* colonies are enumerated for each animals lungs and spleen and corrected for the dilution factor. This value is the number of live tubercle bacilli present in the lungs and spleen of each animal. BCG vaccination typically results in approximately a 1 log reduction in cfu/lung and spleen versus saline vaccination. BCG-DosR vaccination results in a greater reduction of Mtb load in the lungs and spleens of mice.

These studies provide indirect immunological evidence that the DosR regulon over-expressing BCG strain is capable of expressing DosR regulon encoded antigens in vivo and direct evidence that this in vivo expression elicits an immune response as evidenced by antigen-specific T cell responses in mice.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A recombinant *mycobacterium* comprising nucleic acid sequences encoding a DosR protein operably linked to an expression control sequence, wherein said DosR protein is over-expressed in said *mycobacterium* at a level sufficient to cause one or both of a 2 to 100 fold increase in transcription of one or more DosR regulon genes and a 2 to 100 fold increase in translation of one or more DosR regulon proteins encoded by said one or more DosR regulon genes in said *mycobacterium*.

2. The recombinant *mycobacterium* of claim 1, wherein over-expression of said DosR protein is constitutive.

3. The recombinant *mycobacterium* of claim 1, wherein over-expression of said DosR protein is inducible.

4. The recombinant *mycobacterium* of claim 1, wherein said nucleic acid sequences encoding a DosR protein operably linked to an expression control sequence are present on a plasmid.

5. The recombinant *mycobacterium* of claim 1, wherein said nucleic acid sequences encoding a DosR protein operably linked to an expression control sequence are integrated into a chromosome of said recombinant *mycobacterium*.

6. A method for treating latent tuberculosis infection in a patient in need thereof, comprising the step of
administering to said patient a composition comprising
a recombinant *mycobacterium* comprising nucleic acid sequences encoding a DosR protein operably linked to an expression control sequence; and
a physiologically acceptable carrier,
wherein said DosR protein is over-expressed in said *mycobacterium* at a level sufficient to cause one or both of a 2 to 100 fold increase in transcription of one or more DosR regulon genes and a 2 to 100 fold increase in translation of one or more DosR regulon proteins encoded by said one or more DosR regulon genes in said *mycobacterium*,
and wherein said composition is administered in a quantity sufficient to cause said patient to mount an immune response to said one or more DosR regulon proteins encoded by said one or more DosR regulon genes, thereby treating said latent tuberculosis infection.

* * * * *

```
                    SEQUENCE LISTING

<160> NUMBER OF SEQ ID NOS: 4

<210> SEQ ID NO 1
<211> LENGTH: 217
<212> TYPE: PRT
<213> ORGANISM: Mycobacterium tuberculosis

<400> SEQUENCE: 1

Val Val Lys Val Phe Leu Val Asp Asp His Glu Val Val Arg Arg Gly
1               5                   10                  15

Leu Val Asp Leu Leu Gly Ala Asp Pro Glu Leu Asp Val Val Gly Glu
            20                  25                  30

Ala Gly Ser Val Ala Glu Ala Met Ala Arg Val Pro Ala Ala Arg Pro
        35                  40                  45

Asp Val Ala Val Leu Asp Val Arg Leu Pro Asp Gly Asn Gly Ile Glu
    50                  55                  60
```

```
Leu Cys Arg Asp Leu Leu Ser Arg Met Pro Asp Leu Arg Cys Leu Ile
 65                  70                  75                  80

Leu Thr Ser Tyr Thr Ser Asp Glu Ala Met Leu Asp Ala Ile Leu Ala
                 85                  90                  95

Gly Ala Ser Gly Tyr Val Val Lys Asp Ile Lys Gly Met Glu Leu Ala
            100                 105                 110

Arg Ala Val Lys Asp Val Gly Ala Gly Arg Ser Leu Leu Asp Asn Arg
        115                 120                 125

Ala Ala Ala Ala Leu Met Ala Lys Leu Arg Gly Ala Ala Glu Lys Gln
    130                 135                 140

Asp Pro Leu Ser Gly Leu Thr Asp Gln Glu Arg Thr Leu Leu Gly Leu
145                 150                 155                 160

Leu Ser Glu Gly Leu Thr Asn Lys Gln Ile Ala Asp Arg Met Phe Leu
                165                 170                 175

Ala Glu Lys Thr Val Lys Asn Tyr Val Ser Arg Leu Leu Ala Lys Leu
            180                 185                 190

Gly Met Glu Arg Arg Thr Gln Ala Ala Val Phe Ala Thr Glu Leu Lys
        195                 200                 205

Arg Ser Arg Pro Pro Gly Asp Gly Pro
    210                 215

<210> SEQ ID NO 2
<211> LENGTH: 654
<212> TYPE: DNA
<213> ORGANISM: Mycobacterium tuberculosis

<400> SEQUENCE: 2
gtggtaaagg tcttcttggt cgatgaccac gaggtggtgc gtcgtggtct ggttgacttg      60
cttggggccg atcccgagct tgacgtcgta ggtgaggcgg ttcggtcgc cgaggcgatg     120 gccagggttc ctgccgcgcg cccagatgtc gcggtgctgg atgtccggtt gcccgatggc     180
aacggcattg aactgtgccg cgatctgttg tcccgcatgc ccgatctgcg ctgtctgatc     240
ctcacgtcct acacctctga cgaggccatg ctagatgcga ttctcgccgg tgccagcgga     300
tatgtcgtca agacatcaa gggaatggag ttggcgcgcg ccgtcaaaga tgtgggcgct      360
ggacggtcgc tgctggacaa tcgggccgcg gccgcgctga tggccaagct gcgcggtgcc     420
gccgagaagc aggacccgct atcaggcctt accgaccagg agcggacgct actgggcctg     480
cttagcgagg gcctgaccaa caagcagatc gccgaccgaa tgttcctagc cgaaaagacg     540
gtgaagaact acgtgtcgcg gttgctggcc aagctgggca tggaacgtcg gacgcaagcc     600
gcggtattcg cgacggagtt gaagcgctcg cggccacccg gtgatggacc atga           654

<210> SEQ ID NO 3
<211> LENGTH: 33
<212> TYPE: DNA
<213> ORGANISM: Artificial
<220> FEATURE:
<223> OTHER INFORMATION: synthetic oligonucleotide primer

<400> SEQUENCE: 3
gtgcagctgt catggtaaag gtcttcttgg tcg                                   33

<210> SEQ ID NO 4
<211> LENGTH: 32
<212> TYPE: DNA
<213> ORGANISM: Artificial
<220> FEATURE:
<223> OTHER INFORMATION: synthetic oligonucleotide primer
```

```
<400> SEQUENCE: 4
actaagcttc ctgttgtcat ggtccatcac cg                                32
```